United States Patent [19]

Clemens et al.

[11] 4,092,233
[45] May 30, 1978

[54] MEMBRANE APPARATUS

[75] Inventors: Anton Hubert Clemens; Peter Hon Chang, both of Elkhart, Ind.

[73] Assignee: Miles Laboratories, Inc., Elkhart, Ind.

[21] Appl. No.: 683,807

[22] Filed: May 6, 1976

Related U.S. Application Data

[63] Continuation-in-part of Ser. No. 641,978, Dec. 18, 1975, abandoned.

[51] Int. Cl.$^2$ ............................................. G01N 27/46
[52] U.S. Cl. .............................. 204/195 P; 204/195 B; 204/1 T; 195/103.5 R; 195/103.5 C
[58] Field of Search ................ 204/1 P, 1 E, 195 P, 204/195 B; 195/103.5 R, 103.5 C

[56] References Cited

U.S. PATENT DOCUMENTS

| | | | |
|---|---|---|---|
| 3,151,052 | 9/1964 | Arthur et al. | 204/195 F |
| 3,239,444 | 3/1966 | Heldenbrand | 204/195 P |
| 3,334,623 | 8/1967 | Hillier et al. | 204/195 P |
| 3,406,109 | 10/1968 | Molloy | 204/195 P |
| 3,468,781 | 9/1969 | Lucero | 204/195 P |
| 3,539,455 | 11/1970 | Clark | 204/195 P |
| 3,649,504 | 3/1972 | Evans et al. | 204/195 R |
| 3,764,504 | 10/1973 | Arff et al. | 204/195 P |
| 3,887,194 | 6/1975 | Porter et al. | 204/195 P |
| 3,997,420 | 12/1976 | Buzza | 204/195 P |

OTHER PUBLICATIONS

Clark, "Reprint from Annals of the New York Academy of Sciences", vol. 102, Art. 1, pp. 29–45, Oct. 1962.

*Primary Examiner*—T. Tung
*Attorney, Agent, or Firm*—L. E. Davidson

[57] ABSTRACT

An improved apparatus is described wherein a semipermeable membrane is supported against a convex surface and wherein the likelihood of damage to such membrane during mounting and use is minimized. In the apparatus the membrane is stretched over the convex surface of a first member in a manner allowing, during assembly of the apparatus, any fluid located between the membrane and the convex surface to escape therefrom around the edges of the membrane. The membrane is clamped between the convex surface of said first member and a complemental concave surface of a second member such that the membrane is held in stretched relationship against and in close contact with the convex surface. Means is provided to form a fluidtight seal between said membrane and said second member.

In a preferred embodiment, the membrane is used in a polarographic electrode apparatus used to detect specific components of a fluid sample.

3 Claims, 5 Drawing Figures

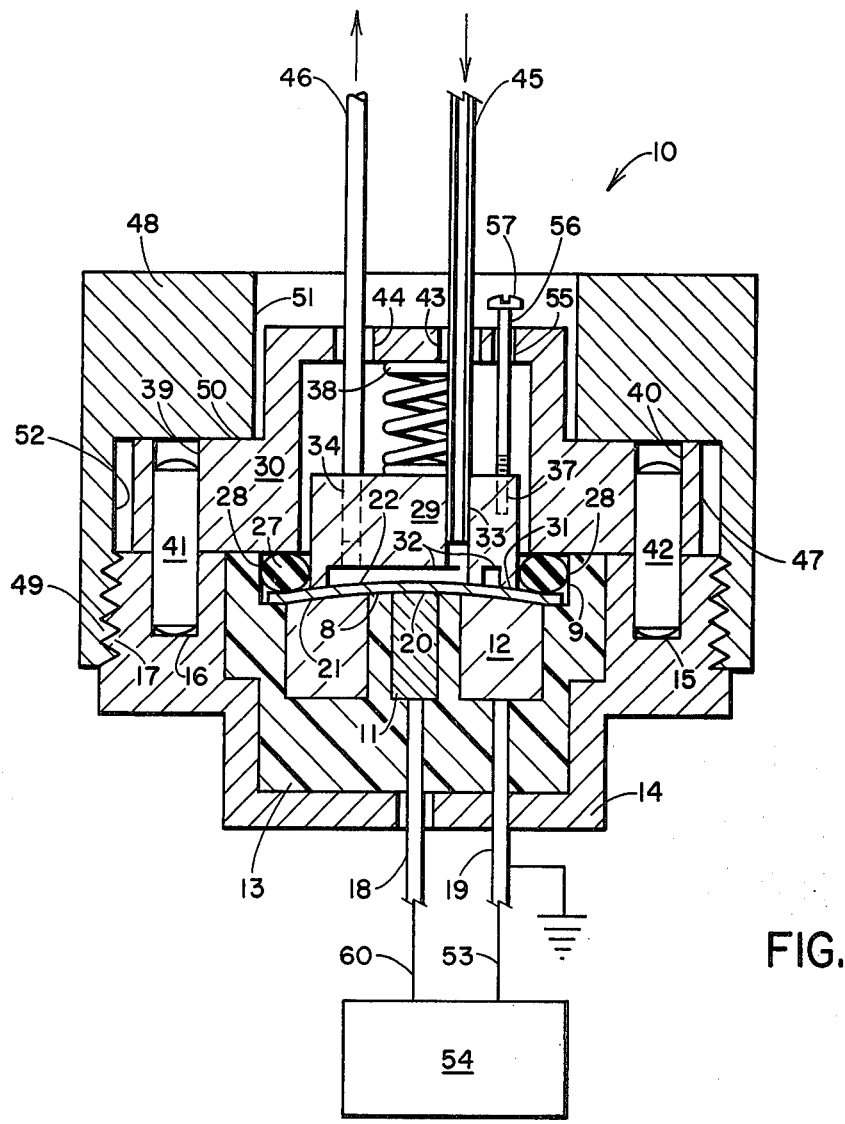
FIG. 1
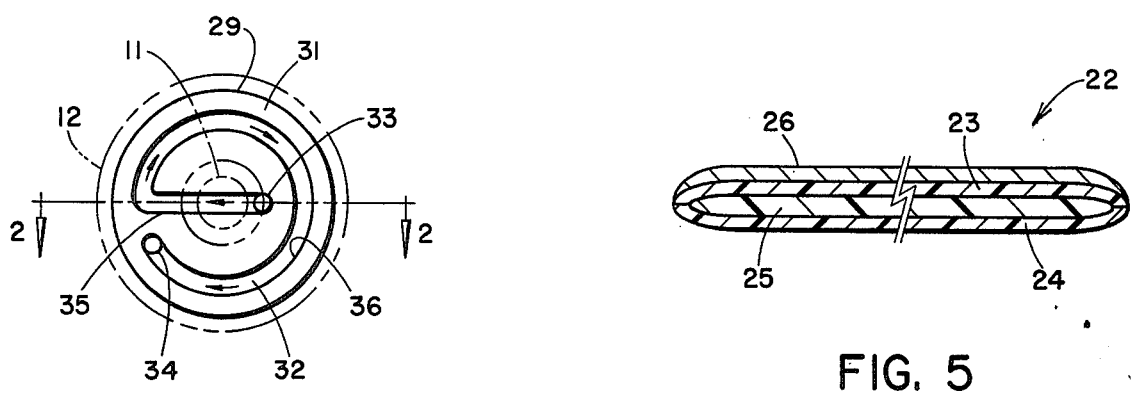
FIG. 2
FIG. 5

MEMBRANE APPARATUS

This application is a continuation-in-part of application Ser. No. 641,978, filed on Dec. 18, 1975, now abandoned.

BACKGROUND AND PRIOR ART

Apparatus employing semi-permeable membranes are employed for various purposes. They are used, for example, in reverse osmosis processes to separate components of a fluid mixture. They are also used in electrode apparatus for the detection and measurement of specific components in a fluid mixture.

One apparatus, for example, previously suggested for the detection and measurement of glucose in body fluids, such as blood, consisted of a sample chamber into which samples were introduced in discrete individual amounts. One side of a semi-permeable membrane containing glucose oxidase was in communication with the same chamber and was capable of allowing portions of the sample in the chamber to pass therethrough. During this passage the glucose oxidase in the membrane catalyzed the oxidation of the glucose in the presence of oxygen in the sample to form hydrogen peroxide. A polarographic anode-cathode assembly was positioned in close proximity to the other side of the membrane and was capable of measuring the amount of hydrogen peroxide formed, thus detecting and measuring the amount of glucose in the sample.

This prior art apparatus had several disadvantages. First, when attempts were made to miniaturize the apparatus, the means for mounting the membrane against the polarographic electrode assembly often caused undesirable rupture of the membrane during mounting or subsequent use. Second, there was often an undesirable slowness in electrode response due to variations in membrane mounting and due to fluids, such as gases, being trapped between the membrane and the electrode assembly. The prior art apparatus was also not capable of handling continuous sampling conditions.

These and other disadvantages of the prior art membrane apparaus are overcome by the apparatus of the present invention.

SUMMARY OF THE INVENTION

In accordance with the present invention, apparatus is provided wherein a membrane is supported in close contact with a surface, said apparatus comprising a first member having a convex surface, a second member having a concave surface facing and complemental to said convex surface, a membrane interposed between said complemental surfaces, and means cooperable with said first and second members for effecting clamping engagement of said membrane between said complemental surfaces whereby said membrane is stretched over and in close contact with said convex surface. During the assembly of this apparatus any fluid located between the membrane and the convex surface is allowed to escape therefrom around the edges of the membrane.

DESCRIPTION OF THE DRAWINGS

FIG. 1 is a vertical cross-sectional view of one illustrative embodiment of apparatus of the present invention employing an electrode assembly with ancillary circuits shown schematically in block diagram form;

FIG. 2 is an end view of the sample chamber member, of the apparatus of FIG. 1;

FIG. 5 is an enlarged fragmentary vertical cross-sectional view of a semi-permeable membrane useful in the apparatus of the present invention.

DESCRIPTION OF THE INVENTION

Figure 3:
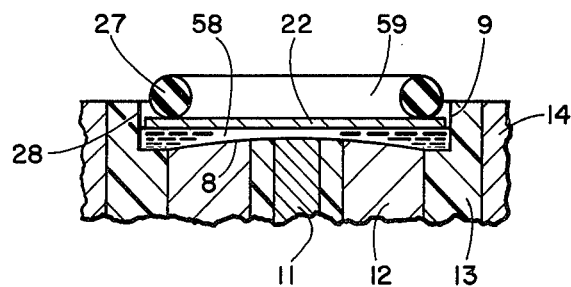
FIG. 3 is a vertical cross-sectional view of a portion of the apparatus of FIG. 1 illustrating one step in the mounting of a membrane used with such apparatus.

Referring to FIG. 1, the apparatus 10 represents an illustrative embodiment of one form of the novel apparatus useful for sensing glucose in a sample fluid. It has a hydrogen peroxide detecting polarographic anode-cathode assembly comprising a central cylindrical anode 11 and a surrounding annular cathode 12 encased in a generally cylindrical insulating first or membrane support member 13. The anode is conveniently formed from platinum and the cathode is conveniently formed from silver. However, other electrically conductive anode and cathode materials can be used. The first member 13 is conveniently formed of an organoplastic material, such as epoxy resin, and is enclosed within a generally cup-shaped electrically conductive case member 14 which is preferably formed of stainless steel. Case member 14 is formed in its end face with diametrically oppositely disposed parallel bores 15 and 16 and is also formed with external threads 17. Electrical conductors 18 and 19 extend from the anode 11 and cathode 12, respectively, through first member 13 and through suitable openings in case member 14. Conductor 18 is preferably insulated by spacing from the case 14, as shown, whereas conductor 19 is preferably in circuit therewith. The upper surfaces 20 and 21 of anode 11 and cathode 12, respectively, are coincident with and form part of a generally convex surface 8 which constitutes the bottom wall of a generally cylindrical recess 9 formed in the upper surface of support member 13. Recess 9 has cylindrical sidewall portion 28 therein.

A circular semi-permeable membrane 22 overlays the convex surface 8, including surfaces 20 and 21. An annular gasket, such as an O-ring 27, is placed on the peripheral edge portions of membrane 22 within the recess 9 as shown. It is convenient to employ a membrane unit in which the O-ring 27 is attached to the membrane 22.

A generally cylindrical second sample chamber or membrane positioning member 29 of smaller diameter than the cylindrical sidewall 28 and having a concave lower end surface 31 facing and complemental to convex surface 8 is positioned on membrane 22 coaxially within the recess 9 and O-ring 27. The concave lower end surface 31 is formed with recess means which may take the form of a groove defining a sample flow passage 32 having a straight diametrically extending portion 35 and a circular portion 36 shown most clearly in FIG. 2. Member 29 has axially extending inlet and outlet passages 33 and 34 therethrough which communicate with the opposite ends of the circuitous passage 32 as shown. The passage 32 and membrane 22 thus form a flow-through sample chamber. The spacial relationship of the anode 11 and cathode 12 to the passage 32 is shown in phantom in FIG. 2. Member 29 is formed from electrically conductive material, such as silver, and is preferably of the same material as cathode 12. In any event, the materials of construction for cathode 12 and member 29 should be so selected as to prevent the formation of an undesirable "half cell". Member 29 also has an internally threaded bore 37.

An inverted cup-shaped sealing member 30 coaxially surrounds and may be in sliding contact with the member 29 and sealingly engages the O-ring 27. An electrically conductive compression spring 38 is located between the sealing member 30 and the member 29. Sealing member 30 has a peripheral flange portion 47 formed with diametrically oppositely disposed bores 39 and 40 which are aligned with the bores 16 and 15 in the case member 14. Alignment pins 41 and 42 may have a press fit respectively in bores 16 and 15 of case member 14 and have a sliding fit within passages 39 and 40, respectively, of sealing member 30. While two alignment pins are shown, it is understood that additional pins and associated bores may also be used if desired. Sealing member 30 is formed with axially extending passages 43, 44 and 55 through the transverse end wall thereof as shown. An electrically conductive inlet tube 45 passes slidably through passage 43 of sealing member 30 and has a sealing fit within the inlet passage 33 of member 29. An outlet tube 46 passes slidably through passage 44 of sealing member 30 and has a sealing fit within outlet passage 34 of member 29. A bolt 56 having a head 57 passes slidably through passage 55 of member 30 and is threaded into bore 37 of member 29 as shown. In FIG. 1, bolt head 57 is located slightly above the transverse wall of member 30.

A clamping nut 48 is formed with an axial bore 51 and a counterbore 52 forming an annular shoulder portion 50. Counterbore 52 has inner threads 49 which are interengageable with external threads 17 on case member 14. As the clamping nut 48 is threaded onto the case member 14, the annular shoulder 50 is moved into mating contact with the flange 47 of sealing member 30 and forces sealing member 30 axially against O-ring 27 while at the same time exerting a compressive axial force on spring 39. The spring 38, in turn, exerts an axial force on the member 29 whereby the membrane 22 is stretched over and into close contact with the convex surface 8 of member 13 by clamping engagement of said membrane between said convex surface 8 and the complemental concave end surface 31 of member 29. This clamping engagement maintains close contact between the membrane and both of said complementary surfaces. The O-ring also forms a liquid-tight seal between the membrane 22 and peripheral portions of the member 29 as well as between the membrane and the recess wall 28. This prevents any loss of liquid from the chamber 32.

Conductors 18 and 19 from the anode 11 and cathode 12, respectively, are connected through lines 60 and 53 to a detecting circuit shown schematically in block 54. The detecting circuit contains an appropriate power supply for the polarographic assembly, as well as indicators controlled by the signals produced by the polarographic assembly.

Conductor 19 may be grounded as shown. It will be observed that the apparatus described includes means providing an electrical connection from the cathode 12, through conductor 19, case 14, nut 48, sealing member 30 and compression spring 38 to the member 29. Other suitable means may be used to effect the electrical connection between the cathode 12 and member 29, for example by the use of a conductor connecting conductor 19 to inlet tube 45, should it be found desirable to form one or more of member 14, nut 48, spring 38 or member 30 of electrically non-conductive material. Thus, the member 29 is maintained at the same electrical potential as the cathode 12. In the disclosed embodiment this potential is preferably ground potential; however, the particular potential maintained is not critical. This arrangement shields the anode from undesirable potentials, such as streaming potentials or static noise, which might otherwise interfere with the polarographic signal. The streaming potentials are neutralized in this arrangement.

The illustrated embodiment of the invention is especially suited for continuous analysis of liquid samples for glucose content. In use, a liquid sample, such as blood, is caused to flow through inlet tube 45, into the flow-through chamber formed by passage 32 and membrane 22, and then out through outlet tube 46. As shown by the arrows in FIG. 2, the sample flows from inlet 33 in a straight line over a small part of the cathode, across the anode and over a part of the cathode, and then continues in an almost completely circular path circumferentially over and along the cathode before exiting from the sample chamber through outlet 34. This flow pattern results in a desirable response time and reduces or prevents undesirable discharges directly over the anode.

The apparatus details of the present invention enable the membrane 22 to be mounted in a manner which minimizes the likelihood of damage during mounting and during subsequent use. This is shown in more detail with reference to FIGS. 3 and 4 which illustrate the manner in which a portion of the apparatus is assembled.

As shown in FIG. 3, which represents a portion of the apparatus of FIG. 1 prior to assembly, the recess 9 is filled with sufficient liquid, such as distilled water or suitable buffer solution 58, to completely cover convex surface 8. The membrane 22, preferably having gasket or O-ring 27 with central opening 59 therein attached thereto, is then floated on liquid 58. The O-ring 27 and membrane 22 fit loosely within the sidewall 28 of recess 9 as shown. The apparatus is then appropriately tilted and tapped so that any air or other gas bubbles initially trapped beneath membrane 22 can escape through the space between the edge of membrane 22 and the recess sidewall 28 and thence through the space between the O-ring 27 and said sidewall. Membrane 22 is preferably sufficiently transparent to allow such bubbles and their movement to be properly observed.

Figure 4:
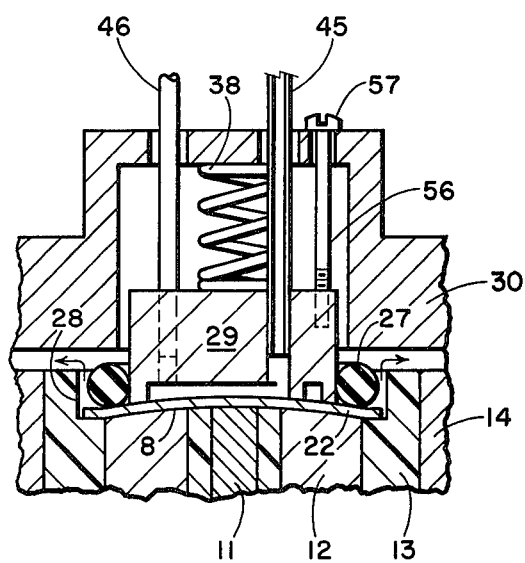
FIG. 4 is a view similar to that of FIG. 3 illustrating a further step in the mounting of the membrane.

The subassembly comprising the members 29 and 30, tubes 45 and 46, spring 38 and bolt 56 is then placed in the coaxial relationship with members 13 and 14 shown in partial cross-section in FIG. 4. Members 29 and 30 are connected by bolt 56, and compression spring 38 forces member 29 away from member 30 until the head 57 of bolt 56 mates against member 30. In the assembly operation member 29 is pushed through opening 59 in O-ring 27 with which it has a snug fit and into contact with membrane 22 forcing said membrane into close contact with convex surface 8 as the concave end surface of member 29 stretches membrane 22 over said convex surface. Such pressure on membrane 22 forces the liquid located beneath membrane 22 out at the periphery of said membrane and through the opening between O-ring 27 and recess sidewall 28. Assembly of the apparatus is completed by application of clamping nut 48 to provide the assemblage shown in FIG. 1. The above apparatus and membrane mounting procedure enables the membrane 22 to be effectively mounted in close contact with the convex surface, such as in a polarographic electrode assembly, while eliminating any undesirable gas bubbles and/or liquid from the space between the membrane and the convex surface. In polarographic electrode systems such undesirable materials can interfere with proper operation. A trapped gas bubble or other fluid could also rupture the membrane during mounting or subsequent use.

When membrane 22 is used in an electrode sensing apparatus, it preferably contains an enzyme to assist in such sensing. One form of membrane useful in the present invention is shown in an enlarged vertical cross-section in FIG. 5. This membrane comprises an upper nucleopore membrane 23, made, for example, of polycarbonate, and a lower membrane 24, made, for example, of cellulose acetate, peripherally joined to form an envelope having a layer of glucose oxidase 25 enclosed therewithin. In a further useful form, the membrane 22 has an electrically conductive coating 26 deposited on the upper surface thereof, for example by vacuum deposition, which coating may be formed, for example, of gold, platinum, palladium, silver, alloys thereof or carbon. The material for coating 26 should be selected so as to prevent the formation of an undesirable "half cell" with cathode 12. It is preferable that coating 26 be of the same material as cathode 12 and member 29. Coating 26 is semi-permeable and preferably has a thickness of about 200 to 400 Angstroms. The nucleopore membrane 23 preferably has an average pore size of about 300 Angstroms prior to application of the coating 26, and the pore size of coating 26 is generally of the same order. It is essential that the coating 26 be "wettable" by the liquid sample material passing through the sample chamber. It has been found that treatment of the coating 26 with an anionic surfactant, such as sodium dodecyl sulfate, renders the coating sufficiently wettable to be used with blood samples. it is understood that other suitable surfactants may also be used.

The electrically conductive coating 26 is in electrical contact with member 29 and thus is at the same potential as cathode 12. This further assists in the elimination of undesirable potentials which might develop during operation.

What is claimed is:

1. Apparatus employing a semi-permeable membrane wherein the membrane is supported against a surface and wherein the likelihood of damage to such membrane during mounting and use is minimized comprising in combination a first member formed with a recess having a cylindrical sidewall and a bottom having a convex surface, a membrane, an annular gasket, a second member having a concave end surface and clamping means, said second member fitting within said gasket and positioning said membrane against said first member wherein said membrane is stretched over said convex surface of said first member by the complemental concave end surface of said second member to effect close contact between said membrane and said convex surface, said annular gasket in an unstressed condition loosely fitting within said cylindrical sidewall of said recess of said first member, any fluid located between said membrane and said convex surface of said first membrane being forced outward by said membrane stretching and being allowed to pass through the space formed by the loose fitting relationship between said annular gasket and said cylindrical sidewall of said first member, said clamping means applying compressive force to said annular gasket and to said second member to form a fluid-tight seal between said cylindrical sidewall of said first member and said second member through said annular gasket and to hold said membrane in stretched relationship against and in close contact with said first member.

2. A glucose sensing apparatus comprising in combination a hydrogen peroxide detecting polarographic assembly having a recess with a convex bottom surface portion and a surrounding cylindrical sidewall, said assembly comprising an anode having a circular end surface and a cathode having an annular end surface in spaced surrounding relation to said anode surface, each of said end surfaces forming part of said convex surface portion of said assembly; a semi-permeable membrane containing glucose oxidase overlying and in close contact with said convex surface; a generally cylindrical electrically conductive flow chamber member having a concave end surface portion formed with flow passage means therein and having inlet and outlet means communicating with said flow passage means, said concave end surface being complemental to and aligned with said convex surface of said polarographic assembly and in overlaying contact with the portion of said membrane in contact with said convex surface, said flow passage means and said membrane forming a flow-through sample chamber providing a sample flow pattern wherein a sample flowing therethrough flows in a straight line over a small portion of said cathode surface, diametrically across said anode surface and thence circumferentially over a substantial portion of said cathode surface before exiting from said sample chamber; an O-ring type sealing means surrounding said flow chamber member and in an unstressed condition loosely fitting within said cylindrical sidewall of said polarographic assembly and in contact with the adjacent upper surface portion of said membrane; an inverted generally cup-shaped sealing member disposed coaxially over said flow-chamber member and having an annular surface engaging said O-ring; means for clamping said sealing member to said polarographic assembly in a manner to effect compression of said O-ring and sealing contact thereof with said chamber member, said cylindrical sidewall of said polarographic assembly and said membrane; compression spring means disposed between said sealing member and said chamber member for biasing the latter axially toward said membrane; and means for effecting an electrical connection between said cathode and said flow chamber member.

3. Apparatus according to claim 2 wherein said cathode and said flow chamber member are formed of the same electrically conductive material.

* * * * *